(12) United States Patent
Golarits et al.

(10) Patent No.: US 11,806,458 B2
(45) Date of Patent: Nov. 7, 2023

(54) BLOOD TREATMENT DEVICE WITH AUTOMATIC REDUCTION OF A SUBSTITUTION-SOLUTION FLOW RATE

(71) Applicant: B. Braun Avitum AG, Melsungen (DE)

(72) Inventors: István Golarits, Budapest (HU); Tibor Osztódi, Budapest (HU); Botond Tényi, Budapest (HU)

(73) Assignee: B. Braun Avitum AG, Melsungen (DE)

( * ) Notice: Subject to any disclaimer, the term of this patent is extended or adjusted under 35 U.S.C. 154(b) by 119 days.

(21) Appl. No.: 17/022,626

(22) Filed: Sep. 16, 2020

(65) Prior Publication Data

US 2021/0077702 A1 Mar. 18, 2021

(30) Foreign Application Priority Data

Sep. 17, 2019 (DE) .................... 10 2019 124 990.2

(51) Int. Cl.
| | |
|---|---|
| *A61M 1/34* | (2006.01) |
| *A61M 1/26* | (2006.01) |
| *A61M 1/16* | (2006.01) |

(52) U.S. Cl.
CPC ............ *A61M 1/3413* (2013.01); *A61M 1/16* (2013.01); *A61M 1/267* (2014.02);
(Continued)

(58) Field of Classification Search
CPC ...... A61M 1/36; A61M 1/341; A61M 1/3672; A61M 1/3434; A61M 1/3437;
(Continued)

(56) References Cited

U.S. PATENT DOCUMENTS

| | | |
|---|---|---|
| 6,406,631 B1 | 6/2002 | Collins et al. |
| 6,730,233 B2 | 5/2004 | Pedrazzi |
| | (Continued) | |

FOREIGN PATENT DOCUMENTS

| | | | | |
|---|---|---|---|---|
| EP | 0829265 B1 | 5/2001 | | |
| EP | 1110566 A2 * | 6/2001 | .......... | A61M 1/0209 |
| | (Continued) | | | |

OTHER PUBLICATIONS

Search Report received in German Application No. 10 2019 124 990.2 dated May 20, 2020, 18 pages.

*Primary Examiner* — Magali P Slawski
*Assistant Examiner* — Robin S Gray
(74) *Attorney, Agent, or Firm* — Christopher A. Rothe; Culhane Meadows PLLC

(57) ABSTRACT

The disclosure relates to a blood treatment device for use in blood treatment therapies, comprising: an extracorporeal blood circuit, a dialyzer and a dialysis fluid circuit, wherein the extracorporeal blood circuit and the dialysis fluid circuit are separated from each other via a membrane provided in the dialyzer, via which blood can be filtered; at least one substitution solution pump, which is configured to supply a substitution solution to the extracorporeal blood circuit before and/or after the dialyzer; an effluent pressure sensor, which is configured to measure a pressure in the dialysis fluid circuit after the dialyzer, and a control unit, which is configured to automatically reduce a flow rate of the at least one substitution solution pump when an effluent pressure measured by the effluent pressure sensor drops during an ongoing blood treatment therapy.

3 Claims, 2 Drawing Sheets

(52) U.S. Cl.
CPC ........ *A61M 1/3403* (2014.02); *A61M 1/3431* (2014.02); *A61M 1/3437* (2014.02); *A61M 2205/18* (2013.01); *A61M 2205/3331* (2013.01); *A61M 2205/505* (2013.01); *A61M 2205/707* (2013.01)

(58) Field of Classification Search
CPC .............. A61M 1/3441; A61M 1/3465; A61M 1/3626; A61M 1/3627; A61M 1/3629; A61M 1/3663; A61M 1/0001; A61M 1/0003; A61M 1/60; A61M 1/30; A61M 1/3331; A61M 1/3334; A61M 1/342; A61M 1/3431; A61M 1/34; A61M 1/3424; A61M 1/1615; A61M 1/1601; A61M 1/1603; A61M 1/1605; A61M 1/1607; A61M 1/1609; A61M 1/1617; A61M 1/1619; A61M 1/16; A61M 1/1613; A61M 1/3403; A61M 1/3413; A61M 1/3635; A61M 1/3609; A61M 1/3639; A61M 2205/3334; A61M 2205/3341; A61M 2205/3351; A61M 2205/3355; A61M 2205/6072; A61M 2205/702; A61M 2205/1647; A61M 2205/707; A61M 2205/7554; A61M 2205/7563; A61M 2205/7581; A61M 2205/50; A61M 2205/502; A61M 2205/505; A61M 2205/3327; A61M 2205/3331; A61M 2230/207; B01D 16/00; B01D 61/243; B01D 61/28; B01D 61/32; B01D 2311/14; B01D 2311/16
See application file for complete search history.

(56) References Cited

U.S. PATENT DOCUMENTS

| | | | |
|---|---|---|---|
| 7,169,352 B1 * | 1/2007 | Felt | A61M 1/3639 210/741 |
| 7,632,411 B2 | 12/2009 | Kuroda et al. | |
| 10,702,643 B2 * | 7/2020 | Wiktor | A61M 1/3666 |
| 11,285,252 B2 * | 3/2022 | Frugier | A61M 1/369 |
| 2002/0023880 A1 | 2/2002 | Pedrini et al. | |
| 2005/0020959 A1 * | 1/2005 | Brugger | A61M 1/3444 604/4.01 |
| 2008/0251433 A1 | 10/2008 | Kim et al. | |
| 2011/0266221 A1 * | 11/2011 | Ware | A61M 1/3441 210/101 |
| 2012/0318739 A1 | 12/2012 | Kopperschmidt et al. | |
| 2013/0303961 A1 * | 11/2013 | Wolff | A61M 1/342 604/5.04 |
| 2014/0102983 A1 * | 4/2014 | Meibaum | A61M 1/1609 210/96.2 |
| 2016/0213829 A1 | 7/2016 | Klewinghaus | |
| 2017/0296726 A1 * | 10/2017 | Riemenschneider | A61M 1/1656 |
| 2017/0312418 A1 * | 11/2017 | Hermann | A61M 1/3653 |
| 2020/0129686 A1 * | 4/2020 | Khawar | A61M 1/1603 |
| 2020/0390954 A1 * | 12/2020 | Rovatti | A61M 1/1656 |
| 2020/0397969 A1 * | 12/2020 | Plahey | A61M 39/08 |

FOREIGN PATENT DOCUMENTS

| | | | | |
|---|---|---|---|---|
| EP | 2504044 B1 | 10/2012 | | |
| EP | 1175917 B2 | 8/2016 | | |
| JP | 3994436 B2 * | 10/2007 | | |
| WO | WO-2016006274 A1 * | 1/2016 | ............. | A61M 1/14 |
| WO | 2018017623 A1 | 1/2018 | | |

* cited by examiner

BLOOD TREATMENT DEVICE WITH AUTOMATIC REDUCTION OF A SUBSTITUTION-SOLUTION FLOW RATE

CROSS-REFERENCE TO RELATED APPLICATION(S)

This application claims priority under 35 U.S.C. § 119 to German Application No. 10 2019 124 990.2, filed Sep. 17, 2019, the contents of which is incorporated by reference herein in its entirety.

FIELD

The present disclosure relates to a blood treatment device, in particular a dialysis device, for use in (continuous) blood treatment/dialysis therapies, in particular renal replacement therapies, comprising: an extracorporeal blood circuit, a dialyzer and a dialysis fluid circuit, wherein the extracorporeal blood circuit and the dialysis fluid circuit are separated from each other via a (semipermeable) membrane provided in the dialyzer, via which blood can be filtered (using a dialysis fluid solution); a plurality of pumps, including at least: a substitution solution pump configured to supply a substitution solution to the extracorporeal blood circuit before and/or after the dialyzer, and preferably an effluent pump provided in the dialysis fluid circuit after the dialyzer/downstream of the dialyzer; and an effluent pressure sensor configured to measure a pressure in the dialysis fluid circuit after the dialyzer/downstream of the dialyzer.

BACKGROUND

Blood treatment devices are already well known. For example, EP 0 829 265 B1 discloses a blood treatment device that comprises an interface for a disposable tubing set, a plurality of pumps such as a blood pump, a syringe pump, an effluent pump and a substitution pump, load cells for measuring the weight of bags containing fluids required for the blood treatment, a user interface comprising a display with touch screen and a control unit for controlling the processes of the blood treatment device. When the control unit in EP 0 829 265 B1 detects that a low pressure is measured in an effluent pressure sensor, the dialyzer/filter is assumed to be clogged and the control unit puts the machine into a safe condition in which all provided pumps are stopped and triggers an alarm.

Another document, EP 2 504 044 B1, also discloses a blood treatment device with a control unit that controls/regulates a flow rate of a substitution solution pump based on a rheological load on the dialyzer. For the determination of the rheological load, a previously calculated transmembrane pressure and a previously calculated flow resistance of the dialyzer/filter are taken into account.

Other documents with background information include U.S. Pat. No. 6,406,631 B1, U.S. Pat. No. 6,730,233 B2, EP 1 175 917 B2, US 2008/0251433 A1, WO 2018/017623 A1, and U.S. Pat. No. 7,632,411 B2.

Conventional blood treatment devices have the disadvantage of having a filter that is either replaced directly when the alarm is issued by the control unit, or that complex calculations, for example of the transmembrane pressure and of the flow resistance of the dialyzer/filter, for the control of the blood treatment device have to be performed to determine a rheological load on the dialyzer.

SUMMARY

It is therefore the object of the present disclosure to avoid or at least reduce the disadvantages of known devices. In particular, the blood treatment device is to be configured in such a way that, in the event of filter clogging or blood clotting, it can extend the service life of the filter/dialyzer with a simple control system.

This object is solved in a generic blood treatment device in that it has a control unit that is configured to automatically reduce a flow rate/delivery rate/delivery quantity of the at least one substitution solution pump if an effluent pressure measured by the effluent pressure sensor drops during an ongoing blood treatment therapy.

In other words, the control unit is configured to monitor (only) the effluent pressure measured by the effluent pressure sensor during the ongoing blood treatment therapy. If the effluent pressure drops, the control unit will not immediately raise an alarm. The blood treatment therapy will not be stopped. The control unit tries to extend the service life of the dialyzer/filter by reducing the flow rate/delivery rate/delivery quantity of the at least one substitution solution pump.

Preferably, the control unit is configured to detect clogging of the dialyzer/filter/membrane or clotting of the blood, solely/only/exclusively in view of the fact/on the basis that the effluent pressure measured by the effluent pressure sensor drops during the ongoing blood treatment therapy.

In other words, a transmembrane pressure and/or a flow resistance of the dialyzer are preferably not taken into account when determining whether a dialyzer is clogged or blood clotting occurs.

In other words, the control unit is preferably configured to set/reduce the flow rate of the substitution solution pump solely/only/exclusively on the basis of the effluent pressure and not on the basis of the transmembrane pressure or of the flow resistance of the dialyzer or any other influencing variable.

Preferably, the control unit is configured to control/set the effluent pressure solely/only/exclusively by changing the flow rate of the at least one substitution solution pump in the event of clogging of the dialyzer or when blood clotting occurs.

The control unit is preferably configured to reduce/change/set/control the flow rate of the at least one substitution solution pump in such a way that a stable effluent pressure is achieved which keeps at least a predetermined distance from a (predetermined) low-pressure warning threshold. The predetermined low-pressure warning threshold represents a limit value. If the effluent pressure falls below this limit value, i.e. if there is low pressure in the effluent pressure, an alarm is raised.

It has been found to be advantageous if the stable effluent pressure is at least 50 mmHg above the low-pressure warning threshold.

It is practical if the blood treatment device has a user interface including a touch screen display and the control unit is set up to show a warning on the display if the effluent pressure drops during therapy and the flow rate of the substitution solution pump is changed/reduced.

Preferably, the control unit is configured to stop the blood treatment therapy and to give an alarm if a flow rate of at least one substitution solution pump falls below a predetermined value.

The predetermined value is preferably set between 25 ml/h and 75 ml/h, in particular at about/approximately 50 ml/h.

Furthermore, it is advantageous if the control unit is configured to increase the flow rate of the substitution solution pump when the effluent pressure returns to a normal pressure range (initial pressure).

The control unit is advantageously configured to reduce the flow rate of the at least one substitution solution pump repeatedly/several times in case that the effluent pressure drops repeatedly/several times in order to maintain the effluent pressure at a predetermined stable effluent pressure or to readjust it to the predetermined stable effluent pressure until the flow rate of the at least one substitution solution pump drops below a predetermined value.

It is practical, when several, in particular two, substitution solution pumps are provided in the blood treatment device and the control unit is configured to stop the blood treatment therapy and to raise an alarm when a flow rate of at least one of the substitution solution pumps falls below a predetermined value.

Preferably, the blood treatment device comprises a weighing device, in particular a load cell, for measuring the weight of a bag, in particular a disposable bag, which contains a solution, for example a substitution solution, required for the blood treatment.

It is practical when the extracorporeal blood circuit and the dialysis fluid circuit are designed as disposable tubes, which are attached to an interface provided on the dialysis device.

Preferably, the plurality of pumps includes at least one blood pump and a syringe pump in addition to the substitution solution pump and the effluent pump.

Furthermore, the blood treatment device is preferably equipped with a bar code reader, which is configured to read bar codes on disposable items such as disposable tubing.

The blood treatment device is preferably configured for wired communication.

The control unit of the blood treatment device is preferably designed as at least one processor, preferably several processors.

In other words, the disclosure relates to a dialysis device. The dialysis device includes a bar code reader. Furthermore, the dialysis device contains a user interface or a display with a touch screen. The dialysis device also has an interface for a disposable tubing set containing a blood side and a dialysis-fluid side separated by a (semi)permeable membrane for filtering blood using a dialysis fluid solution/dialysis solution. A substitution solution/replacement solution is supplied to the blood side before/after a dialyzer. The dialysis device has a blood pump, a syringe pump, an effluent pump, a substitution solution pump etc. The dialysis device is configured for wired communication/has wired or wire-connected communication facilities. The dialysis device is characterized by a software that is particularly suitable for use in continuous dialysis therapies, such as renal replacement therapy. The software runs on a large number of processors within the dialysis device. The dialysis device also has an energy management device (integrated circuit). The dialysis device also contains weighing devices, in particular load cells, which measure the weight of disposable bags containing the fluids (e.g. dialysis fluid solution, substitution solution) required for the dialysis therapy.

The blood treatment device/its control unit provides an automatic reduction of a substitution-solution flow rate. The control unit is configured to adjust the volume of substitution fluid in case of clogging of the dialyzer/filter or blood clotting. If the effluent pressure drops during therapy, the control unit/system automatically reduces the flow rate of the substitution fluid/substitution solution in order to achieve a stable effluent pressure that is at least 50 mmHg above an effluent low-pressure warning threshold. In this case, a warning is displayed on the display/touch screen. The control of the supply of substitution solution can also include a distribution of the supply of substitution solution upstream and downstream of the dialyzer (pre-dilution and post-dilution). Thus, if applicable, the post-dilution flow rate is increased and if necessary, the pre-dilution flow is also increased. If the flow rate of one of the (substitution solution) pumps falls below 50 ml/h, the machine stops the treatment and raises a low-priority alarm. When the effluent pressure returns to a normal pressure range, the system/control unit compensates the missing fluid volume by increasing the substitution solution flow rate. This control/feature can be activated and deactivated by a service technician.

BRIEF DESCRIPTION OF THE DRAWING FIGURES

The disclosure is further explained with reference to the drawing figures, of which:

DETAILED DESCRIPTION

The figures are merely schematic in nature and serve exclusively for understanding the present disclosure. The same elements are marked with the same reference signs.

Figure 1:
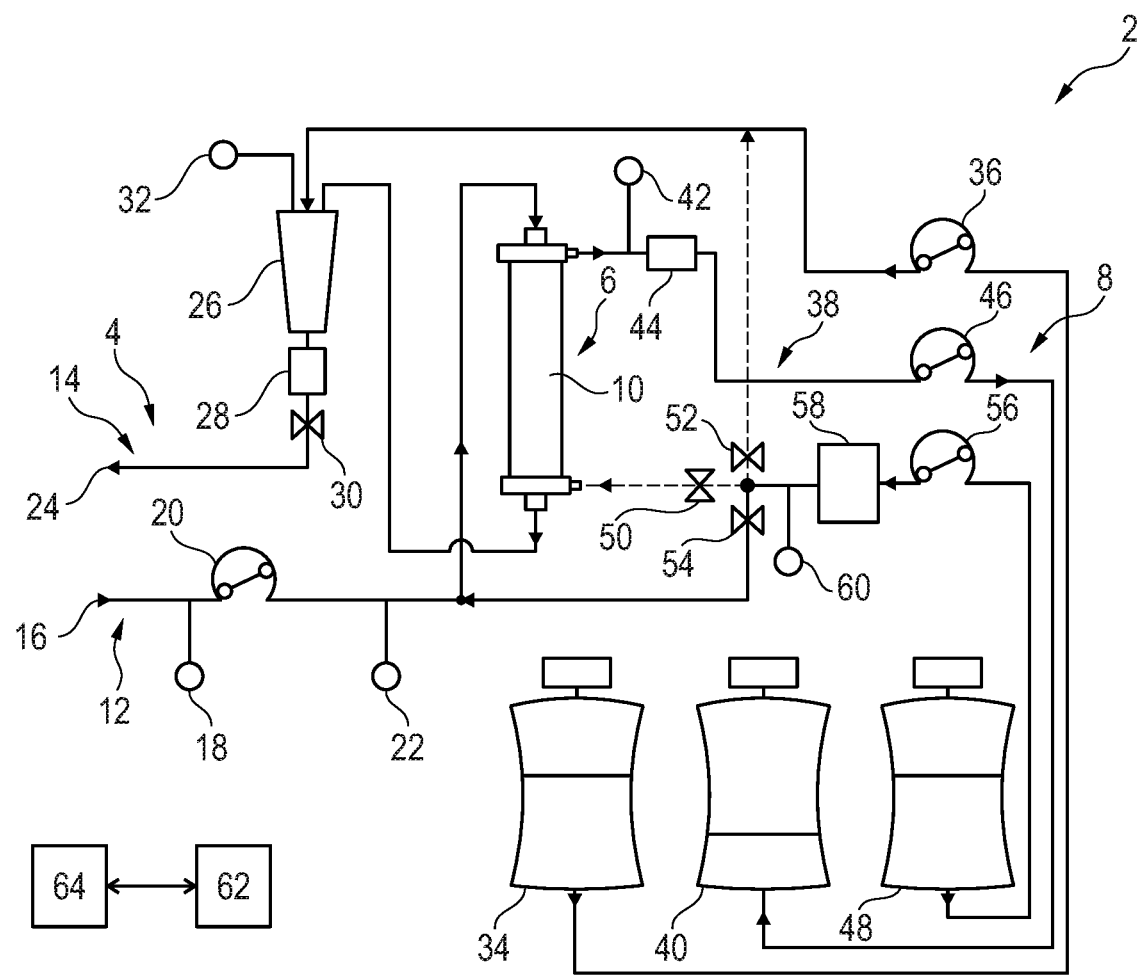
FIG. 1 shows a schematic view of a blood treatment device according to the present disclosure.

FIG. 1 shows a schematic view of an extracorporeal blood treatment device (dialysis device) 2. The blood treatment device 2 is basically configured to be used in both continuous and intermittent blood treatment therapies, in particular renal replacement therapies. The blood treatment device 2 is configured in particular as an acute dialysis machine or an acute dialysis device and is thus essentially prepared for use in intensive care units with predominantly unstable patients. With the blood treatment device 2 of the present disclosure, principally a variety of different blood treatment therapies can be performed (e.g. slow continuous ultrafiltration (SCUF), continuous veno-venous hemofiltration (CVVH), continuous veno-venous hemodialysis (CVVHD), continuous veno-venous hemodiafiltration (CVVHDF), therapeutic plasma exchange (TPE), etc.) as well as dilution modes (e.g., pre-dilution, post-dilution, pre-dilution and post-dilution) and anticoagulation types (e.g., none, heparin, citrate, etc.).

The blood treatment device 2 basically has an extracorporeal circuit 4, a dialyzer (hemofilter) 6 and a dialysis fluid circuit 8. The extracorporeal circuit 4 and the dialysis fluid circuit 8 are separated by a membrane 10 provided in the dialyzer 6, through which blood can be filtered using a dialysis fluid solution or without using a dialysis fluid solution.

The extracorporeal circuit 4 comprises an arterial portion 12 and a venous portion 14. In principle, it is provided that the arterial portion 12, in particular one end thereof, is to be connected or attached to an artery of a patient, in particular an intensive care patient. It is also provided that the venous portion 14, in particular one end thereof, is to be connected or attached to a vein of a patient, in particular an intensive care patient.

The arterial portion 12 has, starting from an arterial end 16 in a blood flow direction towards the dialyzer 6, an arterial pressure sensor 18, an (arterial) blood pump 20, and a dialyzer inlet pressure sensor 22. Starting from the dialyzer 6 in a blood flow direction towards a venous end 24, the venous portion 14 has a venous expansion chamber or air trap 26, a safety air detector 28 and a safety valve 30. A venous pressure can be measured on/behind the venous expansion chamber 26 using a venous pressure sensor 32.

As shown in FIG. 1, the venous expansion chamber 26 is connected to a substitution solution bag/container 34. A substitution solution pump 36 is provided and configured to pump a substitution solution from the substitution solution bag 34 into the extracorporeal blood circuit 4, in particular into the venous portion 14 thereof (into the venous expansion chamber 26).

The dialysis fluid circuit 8 has at least one outlet passage 38 for effluent/used dialysis fluid (dialysate)/another fluid. In principle, the effluent/dialysate/the other liquid can flow through the outlet 38 from the dialyzer 6 to a collecting bag/container 40 for effluent/dialysate/etc. In the outlet 38, an effluent pressure sensor 42, a blood leak detector 44 and an effluent pump 46 are arranged or provided in a direction of flow from the dialyzer 6 to the collecting bag 40.

As can be further seen in FIG. 1, a further bag/container 48 is provided in addition to the substitution solution bag 34 and the collecting bag 40. Depending on the desired blood treatment therapy to be performed, the bag 48 may contain, for example, a substitution solution/fluid or a dialysis fluid.

When, for example, a hemodialysis/hemodiafiltration treatment etc. is to be carried out with the extracorporeal blood treatment device 2, i.e. a blood treatment therapy in which dialysis fluid flows through the dialyzer 6 and thus a substance transport from the extracorporeal circuit 4 to the dialysis fluid circuit 8 takes place both by diffusion and convection, then the bag 48 contains dialysis fluid. When a first valve 50 is now opened and both a second valve 52 and a third valve 54 are closed, then the dialysis fluid can be pumped to the dialyzer 6 via a pump 56.

When, for example, hemofiltration etc. is to be performed with the extracorporeal blood treatment device 2, i.e. a blood treatment therapy in which no dialysis fluid flows through the dialyzer 6 and thus substance transport from the extracorporeal circuit 4 to the dialysis fluid circuit 8 takes place only via convection/filtration, the bag 48 can contain a substitution solution. When the first valve 50 and the second valve 52 are closed and the third valve 54 is opened, the substitution solution can be pumped from the bag 48 into the arterial portion 12 of the extracorporeal circuit 4 (pre-dilution). When the first valve 50 and the third valve 54 are closed and the second valve 52 is opened, the substitution solution can be pumped from the bag 48 into the venous portion 14 of the extracorporeal circuit 4 (post-dilution). When the first valve 50 is closed and the second valve 52 and the third valve 54 are opened, the substitution solution can be pumped from the bag 48 into both the arterial portion 12 and the venous portion 14 of the extracorporeal circuit (pre-dilution and post-dilution). According to the present disclosure, pre-dilution and post-dilution can also be achieved by pumping the substitution solution from the substitution solution bag 34 via the substitution solution pump 36 into the venous portion 14 of the extracorporeal circuit 4 (post-dilution) and simultaneously pumping the substitution solution from the bag 48 via the pump (substitution solution pump) 56 into the arterial portion 12 of the extracorporeal circuit 4 (pre-dilution).

As shown in FIG. 1, a fluid warmer 58 and a pressure sensor 60 are provided between the pump 56 and the valve assembly consisting of the first valve 50, the second valve 52, and the third valve 54.

The extracorporeal blood treatment device 2 furthermore has a control unit 62, which receives information from the sensors provided in the blood treatment device 2 and which controls the actuators provided in the blood treatment device 2. According to the disclosure, this provides software-supported therapy in particular. The control unit 62 receives in particular information from the arterial pressure sensor 18, the dialyzer inlet pressure sensor 22, the safety air detector 28, the venous pressure sensor 32, the effluent pressure sensor 42, the blood leak detector 44, the pressure sensor 60, etc. The control unit 62 controls in particular the blood pump 20, the safety valve 30, the substitution solution pump 36, the effluent pump 46, the first valve 50, the second valve 52, the third valve 54, the pump 56, the fluid warmer 58, etc. Furthermore, the control unit 62 exchanges information with a user interface 64 designed as a display with touch screen. For example, the control unit 62 may be configured to display a warning on the user interface 64. Furthermore, information entered by a user/operator on the user interface 64 can be transferred to the control unit 62.

The present disclosure essentially relates to a control performed by the control unit 62. When the control unit 62 receives information from the effluent pressure sensor 42 that the effluent pressure drops during an ongoing blood treatment therapy, the control unit 62 will, according to the present disclosure, control the substitution solution pump 36 and/or the pump 56 (if substitution solution is contained in the bag 48 and the pump 56 is a (second) substitution solution pump) to automatically reduce a flow rate/flow/volume flow through the corresponding pump 36 and/or 56.

Figure 2:
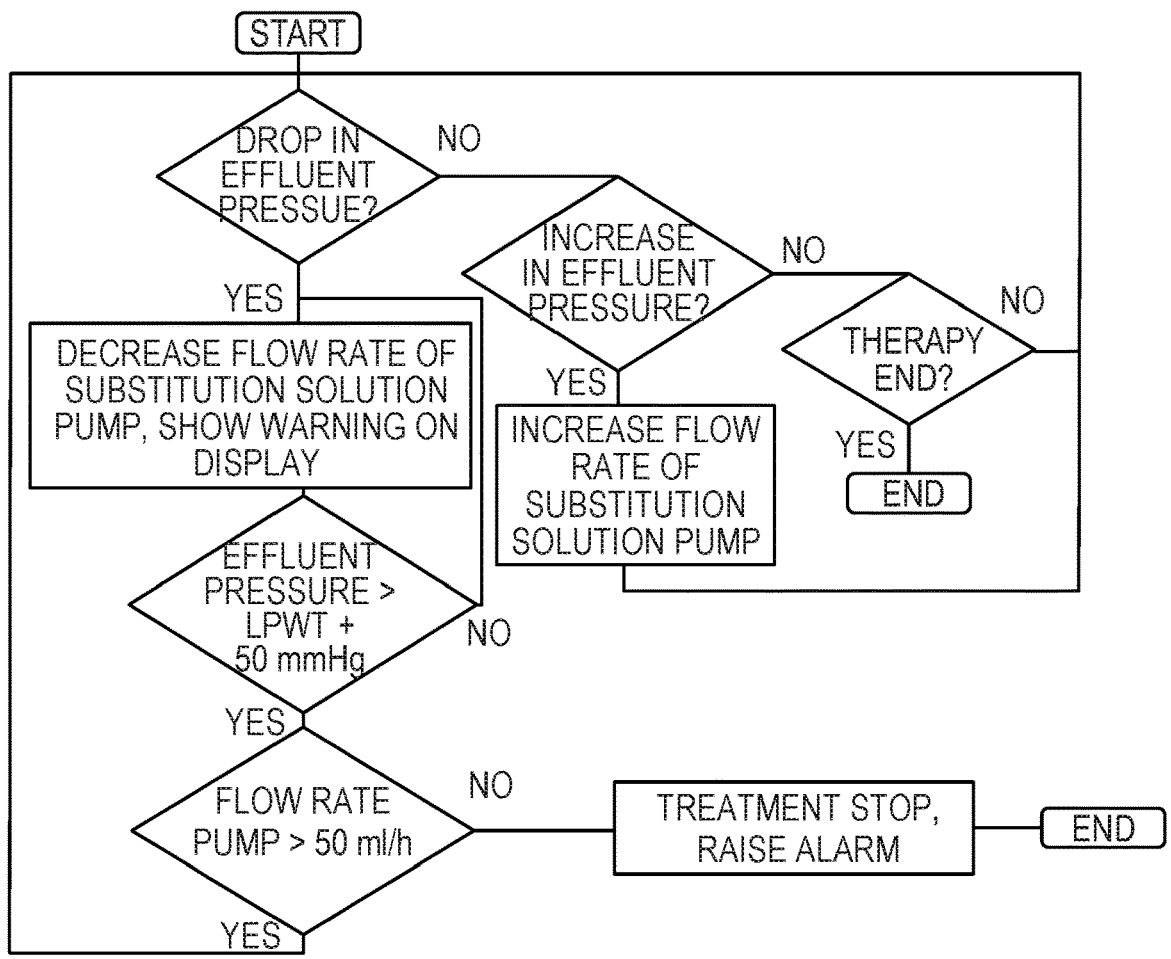
FIG. 2 shows a flow chart illustrating the automatic reduction of a substitution-solution flow rate running in the control unit according to the disclosure.

FIG. 2 shows the sequence of an automatic reduction of a substitution-solution flow rate according to the disclosure, which can be summarized as follows: The control unit 62 of the present disclosure basically receives information from the effluent pressure sensor 42, which monitors a pressure in the dialysis fluid circuit 8 downstream of the dialyzer 6/after the dialyzer 6. When the control unit 62 detects that the effluent pressure drops during an ongoing blood treatment therapy, it concludes that there is clogging of the dialyzer 6 or blood clotting. In order to prolong the service life of the dialyzer/filter 6 in such a case, the control unit 62 reduces a flow rate of at least one substitution solution pump 36, 56, which basically pumps a substitution solution into the extracorporeal blood circuit 4 before and/or after the dialyzer 6. The control unit 62 subsequently checks whether a stable effluent pressure could be achieved by this measure. The stable effluent pressure should be at least 50 mmHg above a predetermined low-pressure warning threshold (limit value below which an alarm is triggered). The control unit 62 then checks whether the flow rate/delivery rate/delivery quantity of the pump 56 and/or of the substitution solution pump 36 is greater than 50 ml/h. If the flow rate of one of the substitution solution pumps is not larger than 50 ml/h, the treatment is stopped, an alarm is raised and the current routine ends. If the flow rate of all substitution solution pumps 36, 56 exceeds 50 ml/h, the control unit 62 monitors whether there is a further drop or an increase in the effluent pressure. If a further drop occurs, the flow rate of the substitution solution pump(s) 36, 56 is further reduced. If an increase occurs, the flow rate of the substitution solution pump(s) 36, 56 is increased accordingly. The present routine also ends when the therapy is finished.

The control system according to the disclosure is explained in detail with reference to the diagram shown in FIG. 3. Here, it becomes clear that the substitution-solution flow rate Q is initially constant and that the effluent pressure p is also constant. The substitution-solution flow rate Q can basically be the flow rate of the substitution pump 36. Furthermore, the substitution-solution flow rate Q can basically also be the flow rate of the pump 56, in particular if the pump 56 works as a substitution solution pump.

At time t1, the control unit 62 (based on the information provided by the effluent pressure sensor 42) detects that the effluent pressure drops during the ongoing blood treatment therapy and the control unit 62 drives the substitution solution pump 36 or the pump 56 or both pumps 36, 56 to reduce the substitution-solution flow rate Q. At the same time, the control unit 62 issues a warning on the user interface 64. As can be seen in FIG. 3, the reduction of the substitution-solution flow rate Q from time t1 onwards ensures that the effluent pressure is set to a stable value/a stable effluent pressure (marked with ① in FIG. 3). This stable effluent pressure has in the present case a distance Δp to a low-pressure warning threshold, which is marked with ② in FIG. 3. According to the present disclosure, Δp is preferably at least 50 mmHg, i.e. the stable effluent pressure ① is at least 50 mmHg greater than the low-pressure warning threshold ②.

Figure 3:
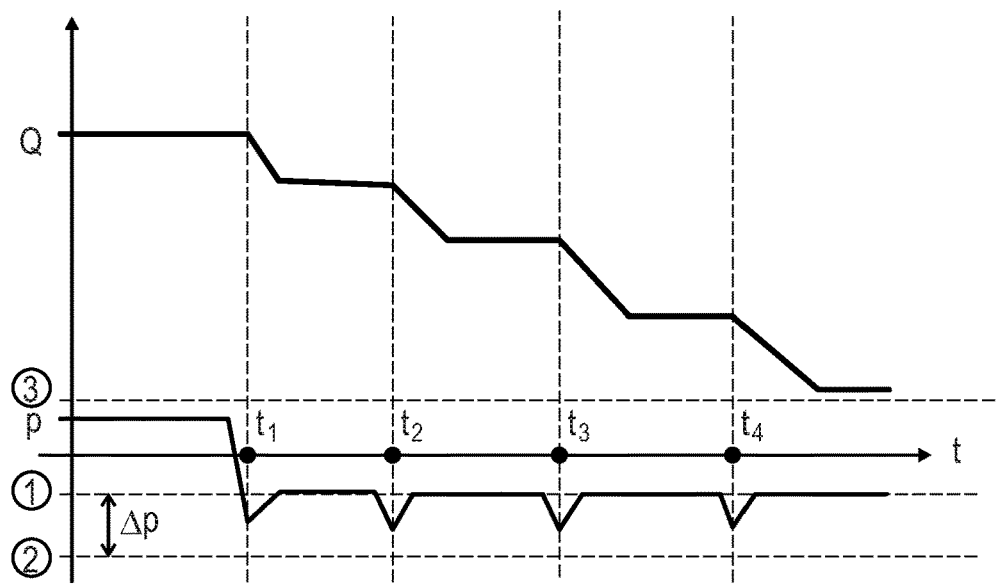
FIG. 3 shows a diagram illustrating the substitution-solution flow rate and an effluent pressure over time according to the present disclosure.

According to the present disclosure, it has been found in particular that, if the aforementioned minimum distance Δp is kept between the stable effluent pressure ① and the low-pressure warning threshold ②, in the event of a renewed drop in effluent pressure, which is determined by the control unit 62 at t2 in accordance with FIG. 3, the control unit 62 can react in due time and further reduce the substitution-solution flow rate Q before the low-pressure warning threshold ② is undercut. Thus, even if the effluent pressure drops again, according to the present disclosure a timely reaction of the control unit 62 allows the effluent pressure to return to the stable effluent pressure ①. In other words, the control according to the disclosure ensures that the low-pressure warning threshold ② is not undercut. The same occurrence as at for time t2 can be observed at times t3 and t4 in FIG. 3.

The control unit 62 further checks, in accordance with the control according to the disclosure, in particular when the effluent pressure has returned to the stable effluent pressure ①, whether the substitution-solution flow rate Q is still above a predetermined value, which is designated with ③ in FIG. 3. As long as this is the case, the blood treatment therapy is continued according to the disclosure. Only if the predetermined value ③ is undershot by at least one substitution solution pump 36, 56 will the treatment be stopped and will an alarm be raised.

According to the disclosure, it has been found that the predetermined value should preferably be set at 50 ml/h. If the substitution-solution flow rate Q of at least one substitution solution pump 36, 56 falls below this value, it is to be assumed in particular that the dialyzer 6 has become clogged in the meantime in such a way that the blood treatment therapy should not be continued. In particular, the dialyzer 6 should be replaced before resuming the blood treatment therapy.

What is claimed:

1. A blood treatment device for use in a blood treatment therapy, the blood treatment device comprising:
    an extracorporeal blood circuit, a dialyzer and a dialysis fluid circuit, the extracorporeal blood circuit and the dialysis fluid circuit separated from each other via a membrane provided in the dialyzer, via which blood is filterable;
    at least one substitution solution pump, which is configured to supply a substitution solution to the extracorporeal blood circuit before and/or after the dialyzer;
    a collection container in the dialysis fluid circuit for collecting effluent from the dialyzer;
    a fluid warmer arranged in the dialysis fluid circuit upstream of the dialyzer;
    a first pressure sensor arranged between the fluid warmer and the dialyzer for measuring a first pressure downstream of the fluid warmer;
    a second pressure sensor arranged between the dialyzer and the collection container for measuring a second pressure downstream of the dialyzer; and
    a control unit configured to automatically reduce a flow rate of the at least one substitution solution pump when the control unit detects a drop in the second pressure measured by the second pressure sensor during the blood treatment therapy,
    wherein the control unit is configured to stop the blood treatment therapy and to raise an alarm when the flow rate of the at least one substitution solution pump falls below a predetermined value.

2. The blood treatment device according to claim 1, wherein the predetermined value is set between 25 ml/h and 75 ml/h.

3. A blood treatment device for use in a blood treatment therapy, the blood treatment device comprising:
    an extracorporeal blood circuit, a dialyzer and a dialysis fluid circuit, the extracorporeal blood circuit and the dialysis fluid circuit separated from each other via a membrane provided in the dialyzer, via which blood is filterable;
    at least one substitution solution pump, which is configured to supply a substitution solution to the extracorporeal blood circuit before and/or after the dialyzer;
    an effluent pressure sensor configured to measure an effluent pressure in the dialysis fluid circuit after the dialyzer; and
    a control unit configured to automatically reduce a flow rate of the at least one substitution solution pump in response to the control unit detecting a drop in the effluent pressure measured by the effluent pressure sensor during the blood treatment therapy,
    wherein the at least one substitution solution pump comprises a plurality of substitution solution pumps, and wherein the control unit is configured to stop the blood treatment therapy and to raise an alarm when a measured flow rate of at least one of the plurality of substitution solution pumps falls below a predetermined value.

* * * * *